(12) United States Patent
Derksen (10) Patent No.: US 6,228,037 B1
(45) Date of Patent: May 8, 2001

(54) METHOD AND APPARATUS FOR THE RECORDING AND ANALYSIS OF RESPIRATORY SOUNDS IN EXERCISING HORSE

(75) Inventor: Frederik J. Derksen, Bath, MI (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 0 days.

(21) Appl. No.: 09/358,033

(22) Filed: Jul. 21, 1999

(51) Int. Cl.[7] ....................................................... A61B 5/08
(52) U.S. Cl. ................................................................ 600/529
(58) Field of Search .................................... 600/529, 459, 600/528, 481

(56) References Cited

U.S. PATENT DOCUMENTS

| 3,990,435 | * 11/1976 | Murphy ................................. 600/529 |
| 4,218,584 | 8/1980 | Attenburrow . |
| 4,720,866 | 1/1988 | Elias et al. . |
| 5,165,417 | 11/1992 | Murphy, Jr. . |
| 5,503,141 | 4/1996 | Kettl et al. . |
| 5,737,429 | 4/1998 | Lee . |
| 5,853,005 | * 12/1998 | Scanlon ................................. 600/459 |

* cited by examiner

Primary Examiner—Cary O'Connor
Assistant Examiner—Brian Szmal
(74) Attorney, Agent, or Firm—Ian C. McLeod (57) ABSTRACT

The present invention is a portable recording unit (10) which allows for recording the respiratory sounds of a horse (100) while the horse is exercising. The recording unit includes a portable microphone (12) connected to a recorder (16). The microphone is mounted by a support bar (14) to the forehead (102A) of the horse such that the head (12A) of the microphone is adjacent the nostrils (108) of the horse. The recorder is attached to the neck (104) of the horse. The portable microphone and recorder allow for recording of the upper airway respiratory sounds without having to transport the horse to a facility. Alternatively, the horse can be positioned on a treadmill (110) and the recorder can be separate from the exercising horse.

7 Claims, 5 Drawing Sheets

METHOD AND APPARATUS FOR THE RECORDING AND ANALYSIS OF RESPIRATORY SOUNDS IN EXERCISING HORSE

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION (1) Field of the Invention

The present invention relates to a method and apparatus for recording the respiratory sounds of a horse during exercise of the horse to determine whether the horse suffers from an upper airway obstruction condition. In particular, the present invention relates to a method and apparatus for recording the respiratory sounds of a horse during exercising by positioning a portable microphone adjacent the horse's nostrils which is connected to a recorder.

(2) Description of the Related Art

Horses commonly suffer from several different upper airway obstructive diseases, including left laryngeal hemiplegia (LLH), dorsal displacement of the soft palate (DDSP), pharyngeal collapse and entrapment of the epiglottis. Left laryngeal hemiplegia and DDSP are by far the most common causes of upper airway obstructions in horses and these conditions have an estimated prevalence of approximately 10% of horses. Left laryngeal hemiplegia is caused by a neuropathy of the left recurrent laryngeal nerve. This condition results in the paresis of the associated arytenoid cartilage. During exercise, this cartilage cause airway obstruction, respiratory noise production and exercise intolerance (Seeherman, H. J., Left Recurrent Laryngeal Neuropathy, In: "Current Therapy in Equine Medicine 4" N. E. Robinson (ed) W. B. Saunders, Philadelphia, pages 404–407 (1997)). The cause of dorsal displacement of the soft palate is presently unknown. Experimentally, the disease is reproduced by blockade of the pharyngeal branch of the vagus nerve. Because this nerve branch runs in close proximity to the retropharyngeal lymph nodes, it is thought that in naturally occurring cases, DDSP is caused by infection of these lymph nodes and consequent damage to the nerve branch. Like in cases with LLH, DDSP causes airway obstruction, respiratory noise production and exercise intolerance in affected horses (Ducharme, N. G. et al, Intermittent Dorsal Displacement of the Soft Palate, In: "Current Therapy in Equine Medicine 4", N. E. Robinson (ed) W. B. Saunders, Philadelphia, pages 415–418 (1997)). In many cases, upper airway conditions can not be diagnosed in the resting horse as the conditions only occur during exercise. Upper airway obstructions are often associated with abnormal respiratory noise. Respiratory sounds in exercising horses are difficult to evaluate because the trained observer is not always in an optimal location. Furthermore, the respiratory sounds are obscured by extraneous noises such as hoof beats, wind noise, or sounds associated with treadmill operation. Presently, diagnostic methods are time consuming, highly technical, and expensive. The old method of diagnosing upper airway conditions in horses involves fiber optic endoscopy. In this technique, a fiber optic endoscope is inserted in the horse's nose and observations are made. To diagnose upper airway conditions that are only apparent during exercise, the horse is exercised on a high-speed treadmill and endoscopy is performed during exercise. This method is highly technical, and can only be performed in referral centers.

In human medicine, spectrogram analysis of speech is a large field of study, and practical applications of this field, including speech therapy and voice recognition, are now commonplace (Kent, R D, Vocal Tract Acoustics, "J. Voice", 7:97–117 (1993)). In addition, spectrogram analysis of sound has been used in many animal species, including songbirds (Lindell C., Limited Geographic Variation in the Vocalizations of a Neotropical Furnariid, *Synallaxis albescens* "Wilson Bull", 110:368–374 (1998)) and marine mammals (Hanggi, E B, Schusterman, R J, Underwater Acoustic Displays and Individual Variation in Male Harbour Seals, *Phoca vitulina,* "Anim. Behav.", 48:1275–1283 (1994)).

Respiratory sounds of horses have been recorded using a radiostethoscope (Attenburrow et al, Resonant Frequency of the Lateral Ventrical and Saccule and "Whistling", "Equine Exerc. Physiol.", pages 27–32 (1990)). These sounds were analyzed using spectrogram analysis. However, respiratory sounds recorded using a radiostethoscope placed over the trachea do not directly relate to the respiratory sounds of exercising horses.

In the related art, U.S. Pat. No. 4,218,584 to Attenburrow describes a stethoscope for detecting and recording data from a horse while the horse is walking, trotting, cantering, jumping and galloping. The invention includes a transducer, such as a microphone which is attached to the animal's skin adjacent the windpipe. The electrical output from the transducer is transferred to a radio transmitter mounted on the animal or its harness. The radio transmitter can transmit signals a distance from the horse to allow for monitoring the breathing at a distance.

Also, of interest is U.S. Pat. No. 4,720,866 to Elias et al which describes a method and apparatus for acquiring, analyzing and displaying stethoscopic data using a microcomputer. The stethoscopic data come from lung sounds, not upper airway sounds as recorded in the invention described therein. The invention includes a means for providing an audio signal. The audio signal is pre-amplified and conditioned for application to a bank of fixed-center-frequency electronic filters. The output of each filter is sampled and converted to digital form. The output is then processed in a computer for analysis and display on a CRT screen or recording in a hard copy device.

U.S. Pat. No. 5,165,417 to Murphy, Jr. describes a diagnostic method and apparatus for detecting breathing abnormalities in humans to diagnose lung (not upper airway) disorders. The system includes means for receiving the sound signal from the patient, means for conditioning the sound signal to attenuate normal sounds and means for storing a sample sound signal. The system may also include means for digitizing the sound signal, means for amplifying the sound signal, means for determining an average signal value of at least a portion of the sound signal, and means for generating a threshold value based on that average value. Further included may be means for sequentially comparing the sound waves with the predetermined time interval to identify an initial deflection wave having a duration falling within the time interval, means responsive to the means for sequentially comparing the sound waves, for sequentially comparing the sound waves following the initial deflection wave to the threshold value, and means for identifying an adventitious sound occurring within the sound signal only when a plurality of consecutive sound waves including the initial deflection wave have an amplitude at least as large as the threshold value.

U.S. Pat. No. 5,737,429 to Lee describes a portable, visible and audible stethoscope. The stethoscope includes a sound absorbing cup having a microphone and an output device. In use, the sounds from the human body are converted into electrical signals by microphone. The electrical signals are amplified in the output device and supplied to the speaker of the output device to produce an audio signal. The amplified electrical signals are also supplied to the oscilloscope to produce a graph representing the electrical signals.

Only of minimal interest is U.S. Pat. No. 5,503,141 to Kettl et al which shows a microphone mounting structure which permits conversion of a conventional respirator into a sound amplifying respirator. The invention uses a microphone responsive to oral sounds within the respiratory mask and produces electrical signals indicative of these oral sounds. The system also includes an amplification circuit which provides output sounds representative of the oral sounds which the microphone detects within the mask.

There remains the need for a method and apparatus for recording the upper airway respiratory sounds of a horse during exercise which is portable and easy to use and which allows for analysis of the respiratory sounds to determine whether the horse has an upper airway condition.

SUMMARY OF THE INVENTION

The present invention is a portable recording unit which allows for recording the upper airway respiratory sounds of a horse while the horse is exercising. The recording unit includes a portable microphone connected to a recorder. The microphone is mounted by a support bar to the forehead of the horse such that the head of the microphone is adjacent the nostrils of the horse. The recorder is attached to the neck of the horse. The portable microphone and recorder allow for recording of the respiratory sounds without having to transport the horse to a facility. Alternatively, the horse can be positioned on a treadmill and the recorder can be separate from the exercising horse.

The substance and advantages of the present invention will become increasingly apparent by reference to the following drawings and the description.

DESCRIPTION OF THE PREFERRED EMBODIMENTS

The present invention relates to an apparatus for recording respiratory sounds of an exercising horse which comprises: a microphone with a head which detects respiratory sounds at close proximity; support means for the microphone mountable on a head of the horse which allows the head of the microphone to be positioned adjacent to nostrils of the horse so that the respiratory sounds at close proximity from the nostrils of the horse are detected; and recording means for recording the respiratory sounds from the microphone at close proximity from the nostrils of the horse wherein the recording means squelches other sounds at a distance from the nostrils.

Further, the present invention relates to a method for recording and analyzing respiratory sounds of an exercising horse to detect an airway condition which comprises: providing an apparatus for analyzing respiratory sounds of an exercising horse which comprises: a microphone with a head which detects sounds at close proximity; support means for the microphone mountable on the head of the horse which allows the head of the microphone to be positioned adjacent to nostrils of the horse so that the respiratory sounds at close proximity from the nostrils of the horse are detected; and recording means for recording the respiratory sounds from the microphone at close proximity from the nostrils of the horse and squelches other sounds at a distance from the nostrils; mounting the head of the microphone adjacent to the nostrils of the horse; recording the respiratory sounds detected by the head of the microphone with the recording means; and analyzing the respiratory sounds recorded on the recording means to detect the condition.

During exercises, horses make an upper airway respiratory sound. In horses with different airway obstruction conditions, these upper airway respiratory sounds change and importantly, are characteristic for each upper airway obstruction condition. The recording unit 10 of the present invention provides an easy and inexpensive method and apparatus for diagnosing upper airway obstruction conditions in exercising horses.

The recording unit 10 includes a microphone 12 connected to a recorder 16. The microphone 12 is preferably a portable, hand-held microphone similar to the Sony Model F-V9 unidirectional dynamic microphone commercially available from The Sony Corporation. The recorder 16 preferably includes a strong compression circuit which allows for recording the respiratory sounds from the horse 100 while squelching ambient noises. The microphone 12 is connected to the head 102 of the horse 100 by a support bar 14. The length of the support bar 14 is such as to be securely fastened to the head 102 of the horse 100 while positioning the head 12A of the microphone 12 the correct distance from the tip or end of the horse's nose 106. The recorder 16 is preferably constructed such as to be fastened to the neck 104 of the horse 100. Alternatively, when the horse 100 is positioned on a treadmill 110, the recorder 16 can be provided with a bracket 18 for mounting the recorder 16 on the treadmill 110.

Figure 2:
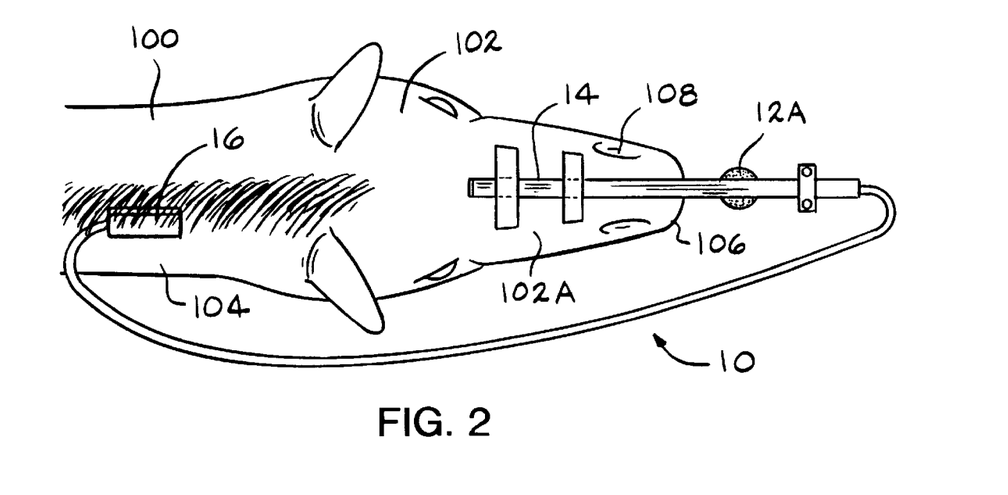
FIG. 2 is a top view showing the support bar 14 mounted on the head 102 of the horse 100 with the recorder 16 mounted along the neck 104 of the horse 100.

In one (1) embodiment, to use the recording unit 10 to record the upper airway respiratory sounds of a horse 100, the microphone 12 is mounted adjacent the horse's nostrils 108 and the recorder 16 is mounted on the neck 104 of the horse 100. To mount the microphone 12 adjacent the nostrils 108 of the horse 100, the microphone 12 is secured to the underside of the support bar 14 adjacent one end of the support bar 14. The microphone 12 is mounted such that the head 12A of the microphone 12 extends inward toward the other end of the support bar 14. The other end of the support bar 14 is then secured to the forehead 102A of the horse 100 such that the support bar 14 extends down along the nose 106 of the horse 100 (FIG. 2). The support bar 14 is preferably fastened to the front of the head 102A of the horse 100 using elastic tape. However, any well known fastener can be used. The support bar 14 is fastened such that the underside of the support bar 14 is adjacent and in contact with the head 102 and nose 106 of the horse 100. The microphone 12 is mounted such that the head 12A of the microphone 12 is in close proximity to the nostrils 108 of the horse 100. The position of the head 12A of the microphone 12 adjacent the tip of the nose 106 of the horse 100 allows for using a "tight-mike" technique to record the respiratory sounds at the nostrils 108 of the exercising horse 100. The recorder 16 is fastened to the neck 104 of the horse 100 by any well known fastening means such as elastic tape. In this embodiment, since the entire recording unit 10 is mounted on the horse 100, the test can be performed anywhere the horse 100 can exercise.

Figure 3:
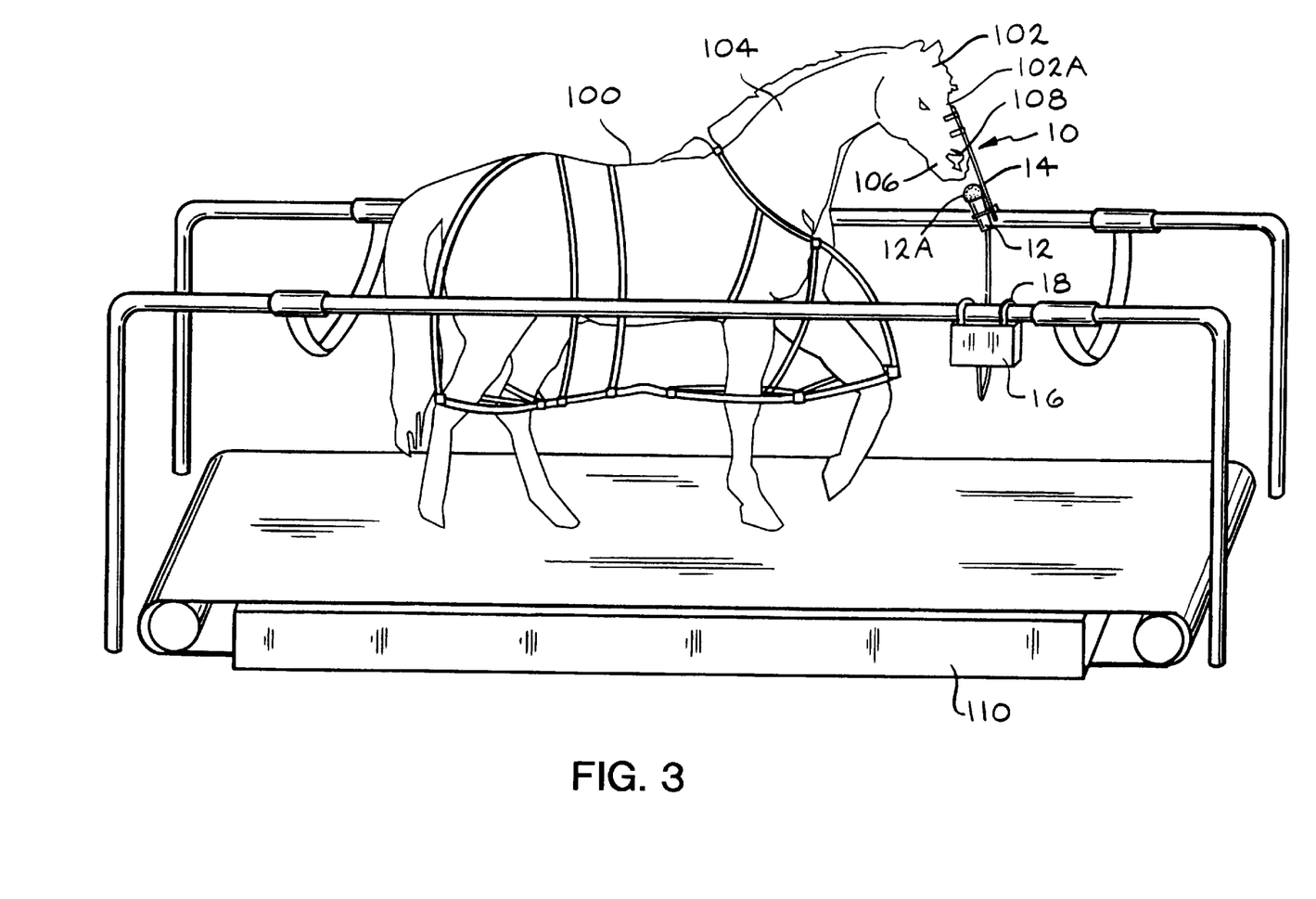
FIG. 3 is a perspective view of the horse 100 exercising on a treadmill 110 with the microphone 12 attached to the head 102 of the horse 100 and the recorder 16 mounted on the treadmill 110.

In an alternative embodiment, the horse 100 is positioned on a high speed treadmill 110 to exercise (FIG. 3). In this embodiment, the recorder 16 can be provided with a bracket 18 which allows for attaching the recorder 16 to the treadmill 110 rather than the exercising horse 100.

Figure 5:
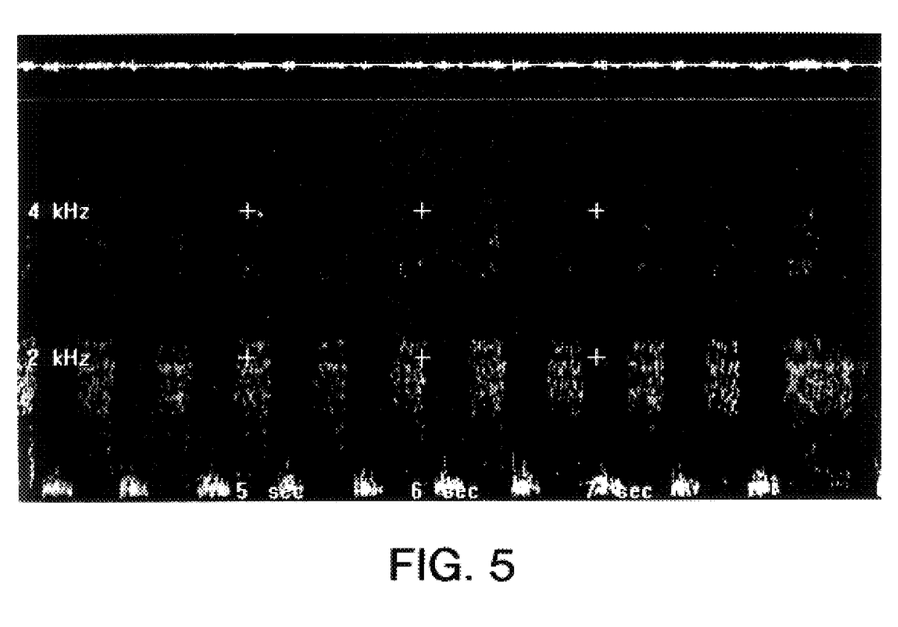
FIG. 5 is a spectrogram of upper airway respiratory sounds of a horse 100 with left laryngeal hemiplegia, exercising on a high speed treadmill 110 at a speed corresponding to maximum heart rate.
Figure 6:
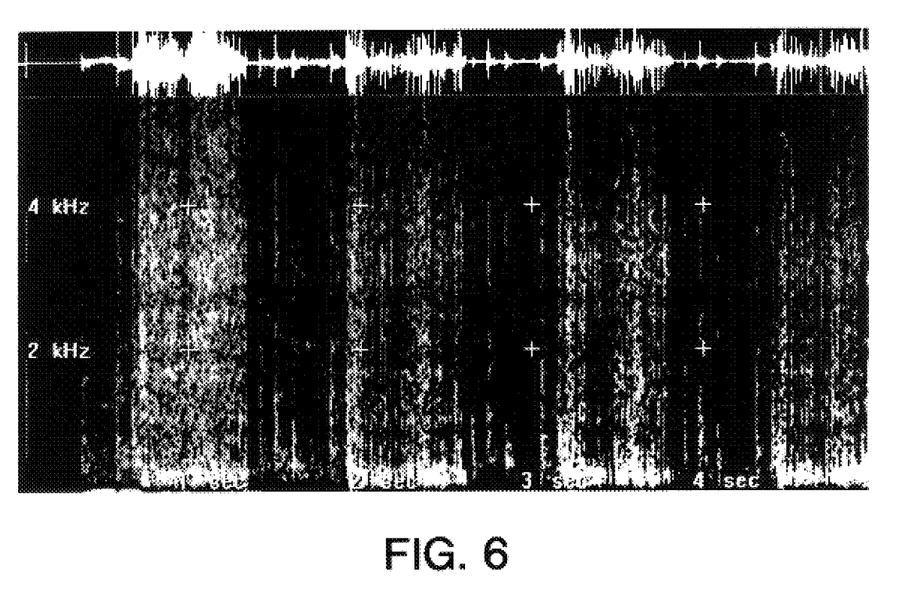
FIG. 6 is a spectrogram of upper airway sounds of a horse 100 with dorsal displacement of the soft palate, exercising on a high speed treadmill 110 at a speed corresponding to maximum heart rate.

After the respiratory sounds are recorded on the recorder 16, the sounds are analyzed using commercially available spectrum analysis computer software and a personal computer (not shown). Spectrum analysis allows plotting of time, frequency and sound amplitude of the respiratory sounds to give easily recognizable patterns. The spectrum analysis patterns associated with various upper airway obstructive conditions such as left laryngeal hemiplegia (LLH) and dorsal displacement of the soft palate (DDSP) are vastly different (FIGS. 5 and 6). The differences in the respiratory sounds and the corresponding spectrum analysis patterns are useful in making a diagnosis of a specific upper airway condition.

EXAMPLE 1

Five (5) Standardbred horses were used in the experiments. Horses were studied under baseline conditions, and after temporary induction of LLH and DDSP using well known local anesthetic techniques (Ehrlich, P J et al, The Effect of Reversible Left Recurrent Laryngeal Neuropathy on the Metabolic Cost of Locomotion and Peak Aerobic Power in Thoroughbred Racehorses, "Vet. Surg." 24:36–48 (1994)) and (Holcombe, S J et al, Effect of Bilateral Blockade of the Pharyngeal Branch of the Vagus Nerve on Soft Palate Function in Horses, "Am. J. Vet. Res." 59:504–508 (1998)). Briefly, to induce LLH, 2 cc of local anesthetic is placed over the left recurrent laryngeal nerve as the nerve approaches the larynx. To induce DDSP, 2 cc of local anesthetic is placed bilaterally over the pharyngeal branches of the vagus nerve as they run through the guttural pouch. A randomized crossover design was used. Studies were separated by at least one week. The speed at which each horse reached maximum heart rate was determined using a rapid incremental exercise test as described in (Holcombe, S J et al, Ibid).

Directly prior to the experiments, the upper airway of each horse was examined using a fiber optic endoscope to ensure that the upper airway functioned normally. Subsequently, the desired experimental condition was created (normal, LLH or DDSP) and verified by endoscopic examination. Next, the recording unit 10 is mounted on the horse 100.

Figure 1:
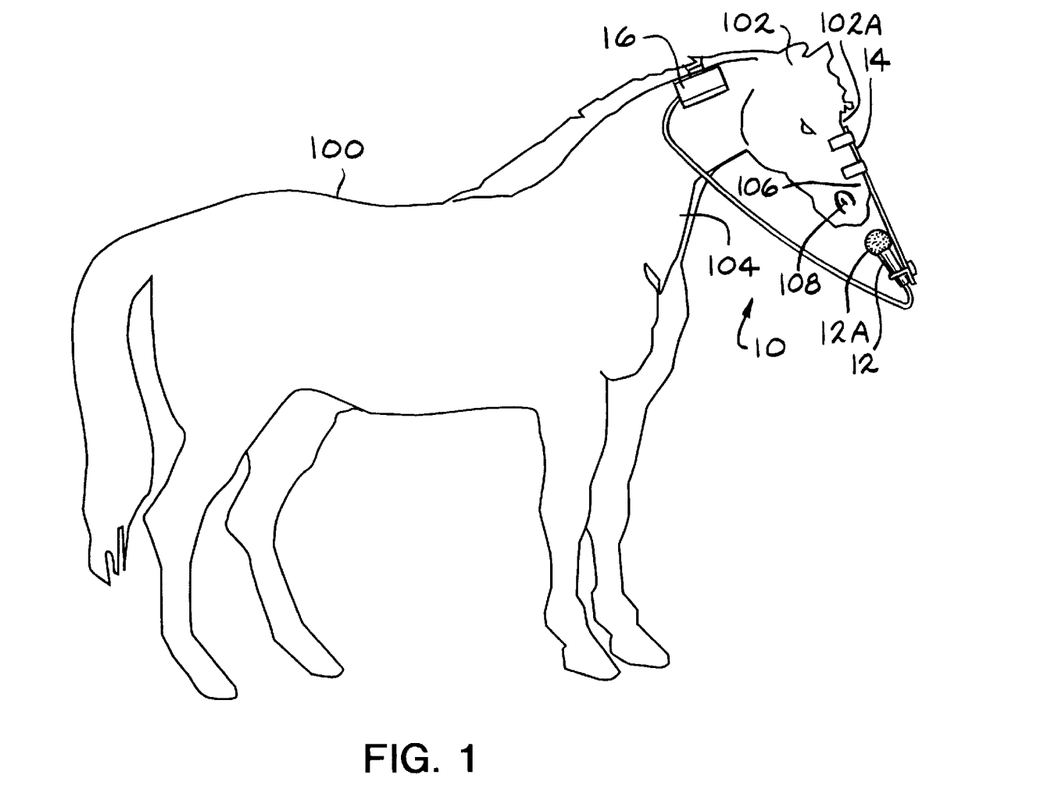
FIG. 1 is a side view showing the microphone 12 and the recorder 16 of the recording unit 10 mounted on the horse 100.

The microphone 12 is fastened by tape to a portion of the support bar 14. The support bar 14 has a length of about 60 cm (24 inches) long. The support bar 14 is secured to the horse's nose 106 with elastic tape (FIG. 1). The microphone 12 is mounted on the underside of the support bar 14 so as to be adjacent the nostrils 108 of the horse 100.

The respiratory sounds of interest are manifested only when a horse 100 is exercising. Therefore, sound recordings are made while the horse 100 is exercising at a speed corresponding to maximum heart rate speed either in the gallop, trot or pace. There is considerable background noise while the recording is made. The ambient noise is rendered harmless by two (2) techniques. First, the recording microphone 12 is unidirectional and is preferably placed about 4.0 cm (1.6 inches) from the tip of the horse's nose 106 ("tight miked"). The microphone 12 is centered on the nose 106 and therefore, is not in the direct path of nasal exhalations. Nevertheless, the microphone 12 is in close proximity to the nostrils 108. The recorder 16 preferably has an automatic gain control. In the preferred embodiment, a Panasonic SLIMLINE® Model RQ2102 was used. The Panasonic SLIMLINE® Model RQ2102 recorder is designed for ready recording of speech in difficult environments such as conference rooms. The input section of the recorder 16 includes a strong compression circuit leading to a constant recording level that promotes intelligibility. The compression system in the recorder 16 is useful because the "tight-miked" exhalations of the horse 100 are intense enough and frequent enough to activate the recorder's compression feature and to squelch the ambient noise. The recorder 16 allows for recording the respiratory sounds from the horse 100 while squelching the environmental noises associated with the exercising horse 100. The microphone 12 is attached by a wire to the recorder 16. The recorder 16 can be mounted on the horse 100 or alternatively, on the treadmill 110.

Once the microphone 12 and recorder 16 are in place, the horses are then placed on a treadmill 110. After a five (5) minute warmup period, the horses 100 were exercised at maximum heart rate for two (2) minutes. Endoscopic examination was repeated immediately following exercise.

Pharyngeal pressure was measured using a pharyngeal catheter positioned at the level of the guttural pouch openings, as described in (Holcombe, S J et al, Ibid). The pharyngeal pressure was used to determine the timing of inhalation and exhalation. The microphone 12 and recorder 16 were then activated. The expiratory sounds of horses 100 were intense enough and frequent enough to activate the compression circuit of the recorder 16, thereby squelching the ambient noise including the environmental noises associated with exercise. The respiratory sounds recorded on the recorder 16 were then analyzed using a computer based spectrogram program. One (1) software program which can be used to analyze the respiratory sounds is AUDIO-SPECTRUM ANALYSIS™, available on the web at http://www.monumental.com/rshorne/gram.html.

Figure 4:
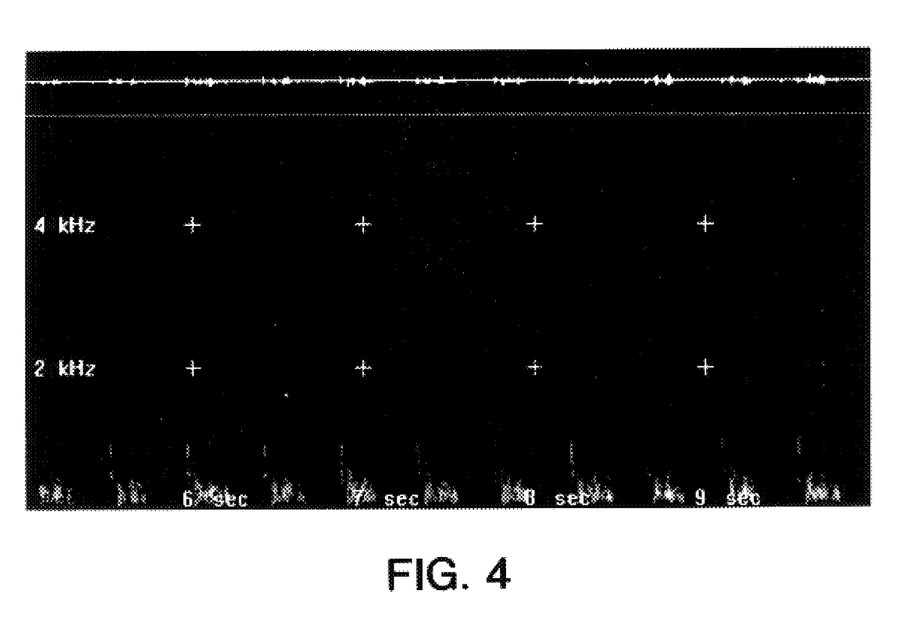
FIG. 4 is a spectrogram of upper airway respiratory sounds of a normal horse 100 exercising on a high speed treadmill 110 at a speed corresponding to maximum heart rate.

The spectrogram pattern of respiratory sounds recorded in exercising horses under baseline conditions, and following induction of LLH and DDSP were markedly different (FIGS. 4 to 6). Under baseline conditions, in horses exercising at a speed corresponding to maximum heart rate, expiratory sounds dominated (FIG. 4). Expiratory sounds occurred in a frequency band ranging from about 70 to 1,500 Hz with peak amplitudes or signal level reaching about 60 decibels. Inspiratory sounds were unapparent. As expected, LLH was associated with inspiratory sounds with a higher frequency (FIG. 5). In horses with LLH, expiratory sounds were unaffected; however, throughout inhalation, the respiratory sound was characterized by a frequency band up to 3,200 Hz and a signal level of approximately 40 decibels. The higher frequency characteristics of the sound explains the "inspiratory whistle" that has been reported in exercising horses with idiopathic laryngeal hemiplegia. DDSP is an expiratory obstruction (Holcombe, S J et al, Ibid). Consequently, respiratory sounds associated with this condition occur during exhalation. In horses with DDSP, inspiratory sounds were similar to those observed in horses exercising under baseline conditions (FIG. 6). In contrast, during exhalation, respiratory sounds were characterized by a broad frequency band up to about 8 KHz and a maximum signal level of about 50 decibels. The respiratory sound during exhalation was not homogeneous but was characterized by rapid reverberations. In horses with DDSP, the sound had a high amplitude, a broad frequency band, and was rapidly periodic. This explains the "rattling" sound frequently described in exercising horses afflicted with DDSP.

Spectrogram analysis of respiratory sounds in exercising horses may have important applications. It appears that all of the upper respiratory conditions of horses are associated with unique spectrogram patterns. Simple recording of respiratory sounds under field conditions can yield a diagnosis of specific upper airway conditions, thereby avoiding the need for endoscopic examinations on a high-speed treadmill. Also, upper airway conditions in horses are associated with exercise intolerance and respiratory noise production.

An additional use of this technology would be to evaluate the efficacy of surgical procedures to treat the upper airway conditions. Presently, the efficacy of surgical conditions to treat upper airway conditions is evaluated using measurements of air flows and driving pressures (Tetens, J. et al, Efficacy of Prosthetic Laryngoplasty with and without Bilateral Ventriculocordectomy as Treatments for Laryngeal Hemiplegia in Horses, "Am. J. Vet. Res.", Vol. 57, No. 11, pages 1668–1673 (1996); Shappell, K. K. et al., Effects of Ventriculectomy, Prosthetic Paryngoplasty, and Exercise on Upper Airway Function in Horses with Induced Left laryngeal Hemiplegia, "Am. J. Vet. Res.", Vol. 49, No. 10, pages 1760–1765 (1988); Belknap, J. K. et al., Failure of Subtotal arytenoidectomy to Improve Upper Airway flow Mechanics in Exercising Standardbreds with Induced Laryngeal Hemiplegia, "Am. J. Vet. Res.", Vol. 51, No. 9, pages 1481–1487, (1990)). Changes in respiratory sounds associated with surgical intervention provides very useful information. In a series of studies, various surgical techniques used to treat these upper airway conditions were evaluated to determine their ability to reduce upper airway impedance (Tetens, J. et al, Ibid; Shappell, K. K. et al, Ibid; Belknap, J. K. et al, Ibid). However, reduction of upper airway impedance in affected horses does not necessarily reduce respiratory noise. For many owners, the respiratory noise associated with upper airway conditions is just as important as the upper airway obstruction. Spectrogram analysis of respiratory sounds in exercising horses now makes it possible to evaluate the efficacy of surgical techniques in reducing respiratory sounds associated with upper airway obstructive conditions.

It is intended that the foregoing description be only illustrative of the present invention and that the present invention be limited only by the hereinafter appended claims.

I claim:

1. An apparatus for recording respiratory sounds of an exercising horse which comprises:

(a) a microphone with a head which detects respiratory sounds at close proximity;

(b) support means for the microphone mountable on a head of the horse which allows the head of the microphone to be positioned adjacent to nostrils of the horse without touching the horse so that the respiratory sounds at close proximity to the nostrils of the horse are detected; and (c) recording means for recording the respiratory sounds from the microphone at close proximity to the nostrils of the horse wherein the recording means squelches other sounds at a distance from the nostrils.

2. The apparatus of claim 1 wherein the support means is a support bar taped to the head of the horse.

3. The apparatus of any one of claims 1 or 2 wherein the microphone is a hand-held type.

4. The apparatus of any one of claims 1 or 2 wherein the recording means has a compression circuit which allows for a constant recording level of the sounds at close proximity to the nostrils of the horse.

5. A method for recording and analyzing respiratory sounds of an exercising horse to detect an airway condition which comprises:

(a) providing an apparatus for analyzing respiratory sounds of an exercising horse which comprises: a microphone with a head which detects respiratory sounds at close proximity; support means for the microphone mountable on the head of the horse which allows the head of the microphone to be positioned adjacent to nostrils of the horse without touching the horse so that the respiratory sounds at close proximity to the nostrils of the horse are detected; and recording means for recording the respiratory sounds from the microphone at close proximity to the nostrils of the horse and squelches other sounds at a distance from the nostrils;

(b) mounting the head of the microphone adjacent to the nostrils of the horse;

(c) recording the respiratory sounds detected by the head of the microphone with the recording means; and (d) analyzing the respiratory sounds recorded on the recording means to detect the condition.

6. The method of claim 5 wherein the analysis is for laryngeal hemiplegia and dorsal displacement of the soft palate.

7. The method of claim 5 wherein a computer program produces a graph of the respiratory sounds for the analyzing in step (d).

* * * * *

US006228037C1

(12) EX PARTE REEXAMINATION CERTIFICATE (5749th)

United States Patent
Derksen (10) Number: US 6,228,037 C1
(45) Certificate Issued: Apr. 24, 2007

(54) METHOD AND APPARATUS FOR THE RECORDING AND ANALYSIS OF RESPIRATORY SOUNDS IN EXERCISING HORSE

(75) Inventor: Frederik J. Derksen, Bath, MI (US)

(73) Assignee: Board of Trustees Operating Michigan State University, East Lansing, MI (US)

Reexamination Request:
No. 90/006,592, Apr. 4, 2003

Reexamination Certificate for:
Patent No.: 6,228,037
Issued: May 8, 2001
Appl. No.: 09/358,033
Filed: Jul. 21, 1999

(51) Int. Cl.
*A61B 5/08* (2006.01)

(52) U.S. Cl. .......................................... 600/529; 600/586
(58) Field of Classification Search .................... None
See application file for complete search history.

(56) References Cited

U.S. PATENT DOCUMENTS

| 5,782,240 A | 7/1998 | Raviv et al. |
| 6,228,037 B1 | 5/2001 | Derksen |

OTHER PUBLICATIONS

Parente, E.J. et al "Upper Respiratory Dysfunctions in Horses During High–Speed Exercise", American Association of Equine Practitioners 40th Annual Convention Proceedings, 1994, pp. 81–82.

D.P. Attenburrow, "Respiratory Sounds recorded by Radio–Stethoscope from Normal Horses at Exercise," Equine Vet. J., 10(3) 176–179 1978.

D.P. Attenburrow, "Time relationship between the respiratory cycle and limb cycle in the Horse" Equine Vet. J. (1982) 14 (1), 69–72.

G.R. Barnes et al. "Sound Spectrography in the Diagnosis of Equine Respiratory Disorders: A Preliminary." New Zealand Vet J.(1979) vol. 27.

Subburaj S., L Parvez et al. "Methods of Recording and Analizing Cough Sounds". Pulmonary Pharmacology (1996) 9 269–279.

Markus, John. "Electronics Dictionary". Fourth Edition. 1978. pp. 44, 124, 615.

Consumer Reports Books. "Guide to Electronics in the Home". 1988. pp. 213–217.

Eargle, John. "Sound Recording". 1976. Van Nostrand reinhold Company. pp. 241–254.

*Primary Examiner*—Robert L. Nasser (57) ABSTRACT

The present invention is a portable recording unit (10) which allows for recording the respiratory sounds of a horse (100) while the horse is exercising. The recording unit includes a portable microphone (12) connected to a recorder (16) The microphone is mounted by a support bar (14) to the forehead (102A) of the horse such that the head (12A) of the microphone is adjacent the nostrils (108) of the horse. The recorder is attached to the neck (104) of the horse. The portable microphone and recorder allow for recording of the upper airway respiratory sounds without having to transport the horse to a facility. Alternatively, the horse can be positioned on a treadmill (110) and the recorder can be separate from the exercising horse.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–5 are cancelled.

Claims 6 and 7 are determined to be patentable as amended.

New claim 8 is added and determined to be patentable.

6. The method of claim [5] *8* wherein the analysis is for laryngeal hemiplegia and dorsal displacement of the soft palate.

7. The method of claim [5] *8* wherein a computer program produces a graph of the respiratory sounds for the analyzing in step (d).

*8. A method for recording and analyzing respiratory sounds of an exercising horse to detect an airway condition which comprises:*

*(a) providing an apparatus for analyzing respiratory sounds of an exercising horse which comprises: a microphone with a head which detects respiratory sounds at close proximity; support means for the microphone mountable on the head of the horse which allows the head of the microphone to be positioned between both nostrils of the horse without touching the horse and out of the direct path of nasal exhalations so that the respiratory sounds at close proximity to the nostrils of the horse are detected; and recording means for recording the respiratory sounds from the microphone at close proximity to the nostrils of the horse and squelches other sounds at a distance from the nostrils;*

*(b) mounting the support means on the head of the horse so that the head of the microphone is positioned between the nostrils of the horse and out of the direct path of nasal exhalations;*

*(c) recording the respiratory sounds detected by the head of the microphone with the recording means; and*

*(d) analyzing the respiratory sounds recorded on the recording means to detect the condition.*

* * * * *